United States Patent
Coenen

(10) Patent No.: US 7,318,343 B2
(45) Date of Patent: Jan. 15, 2008

(54) SYSTEM FOR DETECTING GAS IN A WELLBORE DURING DRILLING

(75) Inventor: Josef Guillaume Christoffel Coenen, Rijswijk (NL)

(73) Assignee: Shell Oil Company, Houston, TX (US)

( * ) Notice: Subject to any disclaimer, the term of this patent is extended or adjusted under 35 U.S.C. 154(b) by 82 days.

(21) Appl. No.: 10/519,137

(22) PCT Filed: Jun. 17, 2003

(86) PCT No.: PCT/EP03/06414

§ 371 (c)(1),
(2), (4) Date: Dec. 22, 2004

(87) PCT Pub. No.: WO2004/003343

PCT Pub. Date: Jan. 8, 2004

(65) Prior Publication Data

US 2005/0241382 A1    Nov. 3, 2005

(30) Foreign Application Priority Data

Jun. 28, 2002 (EP) ................................. 02254596

(51) Int. Cl.
*E21B 47/10* (2006.01)
(52) U.S. Cl. .................. 73/152.19; 73/152.01
(58) Field of Classification Search ............. 73/152.19, 73/152.01, 152.18
See application file for complete search history.

(56) References Cited

U.S. PATENT DOCUMENTS

| 3,595,075 | A | * | 7/1971 | Dower | 73/152.19 |
| 3,802,260 | A | * | 4/1974 | Kishel | 73/152.04 |
| 3,813,935 | A | * | 6/1974 | Tanguy et al. | 73/152.19 |
| 4,370,886 | A | * | 2/1983 | Smith et al. | 73/152.42 |
| 4,546,640 | A | * | 10/1985 | Stone et al. | 73/19.09 |
| 4,867,254 | A | * | 9/1989 | Gavignet | 175/48 |
| 4,887,464 | A | | 12/1989 | Tannenbaum et al. | 73/153 |

(Continued)

FOREIGN PATENT DOCUMENTS

| WO | 01/63094 | 8/2001 |
| WO | 01/98630 | 12/2001 |

OTHER PUBLICATIONS

International Search Report dated Sep. 10, 2003.

(Continued)

*Primary Examiner*—Hezron Williams
*Assistant Examiner*—Rodney Frank

(57) ABSTRACT

A system is provided for detecting the presence of formation gas in a stream of drilling fluid flowing through a wellbore during drilling of the wellbore. The system has at least one sensor chamber connectable to a drill string for drilling the wellbore, each sensor chamber containing a volume of a selected gas and having a membrane wall which allows passage of formation gas from the stream of drilling fluid into the sensor chamber. The sensor is arranged to detect a change of a selected characteristic of the volume of gas due to passage of formation gas from the stream of drilling fluid via the membrane wall into the sensor chamber.

16 Claims, 3 Drawing Sheets

U.S. PATENT DOCUMENTS

| | | | |
|---|---|---|---|
| 5,005,406 A * | 4/1991 | Jasinski et al. | 73/152.19 |
| 5,144,831 A | 9/1992 | Hale et al. | 73/19.05 |
| 5,351,532 A | 10/1994 | Hager | 73/153 |
| 5,469,917 A | 11/1995 | Wolcott | 166/250.01 |
| 5,608,167 A | 3/1997 | Hale et al. | 73/715 |
| 5,979,219 A | 11/1999 | Sellmer-Wilsberg et al. | 73/19.12 |
| 6,272,938 B1 | 8/2001 | Baghel et al. | 73/863.23 |
| 6,675,914 B2 * | 1/2004 | Masak | 175/48 |
| 6,995,360 B2 * | 2/2006 | Jones et al. | 250/269.1 |
| 7,100,689 B2 * | 9/2006 | Williams et al. | 166/264 |
| 2004/0045350 A1 * | 3/2004 | Jones et al. | 73/152.23 |

OTHER PUBLICATIONS

A. O. Brumboiu, et al: "Application of Semipermeable Membrane Technology in the Measurement of Hydrocarbon Gases in Drilling Fluids", Jun. 19, 2000, pp. 1-12, SPE #62525.

Dria, Dennis E. "Membrane-based gas sensing for robust pay identification", 42$^{nd}$ Annual SPWLA Logging Symposium, Jun. 17, 2001, pp. 1-6.

News Release Sandia National Laboratory, "Sandia's Soil and Groundwater Chemical Sniffer" May Help Protect the Nation's Water Supply, http://www.sandia.gov/media/NewsRel/NR2001/watsniff.htm.

Yu M. Conrad et al., "High Performance Hand-Held Gas Chromatograph", Proceedings of the 1998 ASME International Mechanical Engineering Congress and Exposition; Anaheim, CA USA, pp. 481-486. (Abstract Only).

* cited by examiner

Fig.2.
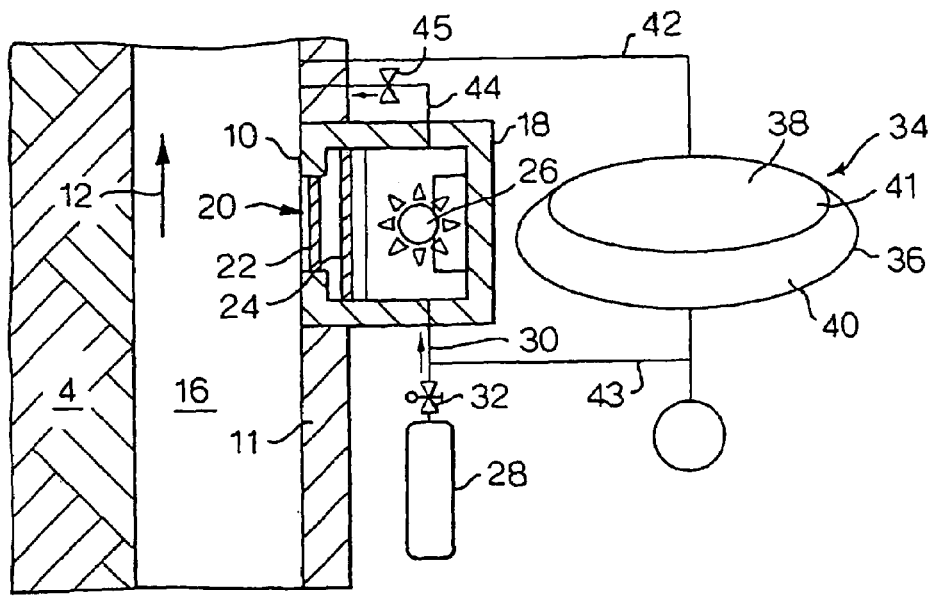
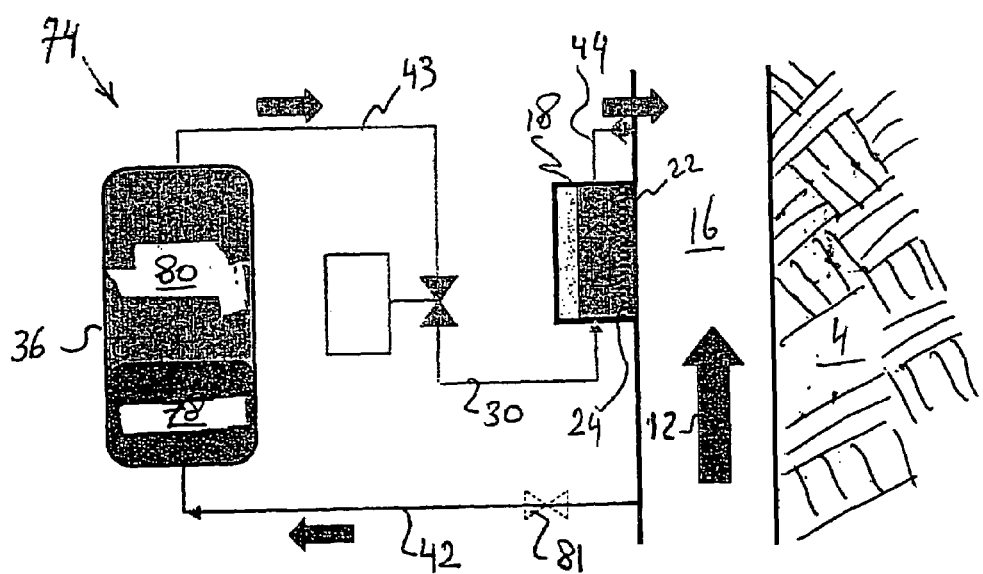
Fig. 3

SYSTEM FOR DETECTING GAS IN A WELLBORE DURING DRILLING

The present application claims priority on European Patent Application 02254596.6 filed 28 Jun. 2002.

BACKGROUND OF THE INVENTION

The present invention relates to a system for detecting the presence of formation gas in a stream of drilling fluid flowing through a wellbore during drilling of the wellbore. In the search for hydrocarbon fluids present in earth formation layers it is important to detect the inflow of gas from the earth formation into the wellbore during drilling, at an early stage. If the gas is at high pressure early detection is crucial to ensure proper well control and to forego inadvertent wellbore conditions. Furthermore, the inflow of gas in the wellbore fluid provides valuable information on the various earth formation layers crossed by the wellbore. Thus, gas inflow may be indicative for hitting a hydrocarbon rich prospect or for an emerging hazardous blowout. Gas species which are most common in earth formation layers are methane ($CH_4$), carbon dioxide ($CO_2$) and nitrogen ($N_2$). Also $H_2S$ may be encountered during wellbore drilling.

These gas species may occur either as free-gas bubbles or as gas dissolved-in-liquid.

Until now it has been difficult to detect the presence of earth formation gases during wellbore drilling in a timely and accurate manner.

SUMMARY OF THE INVENTION

It is therefore an object of the invention to provide a reliable and accurate system for detecting the presence of formation gas in a stream of drilling fluid flowing through a wellbore during drilling of the wellbore.

In accordance with the invention there is provided a system for detecting the presence of formation gas in a stream of drilling fluid flowing through a wellbore during drilling of the wellbore, the system comprising at least one sensor chamber connectable to a drill string for drilling the wellbore, each sensor chamber containing a sensor and a volume of a selected gas and having a membrane wall which allows passage of formation gas from the stream of drilling fluid into the sensor chamber, the sensor being arranged to detect a change of a selected characteristic of said volume of gas due to passage of formation gas from the stream of drilling fluid via the membrane wall into the sensor chamber.

The membrane wall allows gas to pass into the sensor chamber. By detecting the change of the selected characteristic due to gas having passed the membrane, it is achieved that a signal indicative of such gas passage is timely provided.

Preferably, the membrane wall is both hydrophobic and oleophobic. Herewith both oil and water are effectively kept out of the sensing chamber, by virtue of which is possible to provide a Micro-Electro-Mechanical-Sensor solid-state sensor ("MEMS sensor") as the sensor. Such MEMS sensor can be silicon based and/or polymer based. Various types of MEMS sensors can be used, including a thermal conductive sensor, a thermo catalytic sensor, and an electro-chemical sensor, such as a metal-oxide electro-chemical sensor.

In an advantageous embodiment, the system comprises a pressure balancing device arranged to maintain the gas pressure in the sensor chamber substantially equal to the fluid pressure in the stream of drilling fluid. Due to the low pressure difference between the gas in the sensor chamber and the fluid pressure in the well bore, the membrane wall can have a low break-through pressure which is advantageous for the response time of the system to changes in concentration of formation gas in the drilling fluid. Moreover, since the gas pressure is balanced with the fluid pressure, the system is suitable for use at any depth.

In a particular advantageous embodiment of the invention, the system comprises a first said sensor chamber and a second said sensor chamber, and wherein the gas supply device includes means for supplying a first said selected gas to the first sensor chamber and means for supplying a second said selected gas to the second sensor chamber. Each of the sensor chambers has its own individual response to the presence of formation gas of a certain type, allowing for down hole compositional analysis of formation gas by combining the sensor signals.

BRIEF DESCRIPTION OF THE DRAWING

The invention will be described hereinafter in more detail and by way of example with reference to the accompanying drawings in which:

FIG. 2 schematically shows a detail of the system of FIG. 1;

FIG. 3 schematically shows an alternative pressure balancing device for the system of FIG. 1.

In the Figures like reference numerals relate to like components.

DETAILED EMBODIMENT OF THE INVENTION

Figure 1:
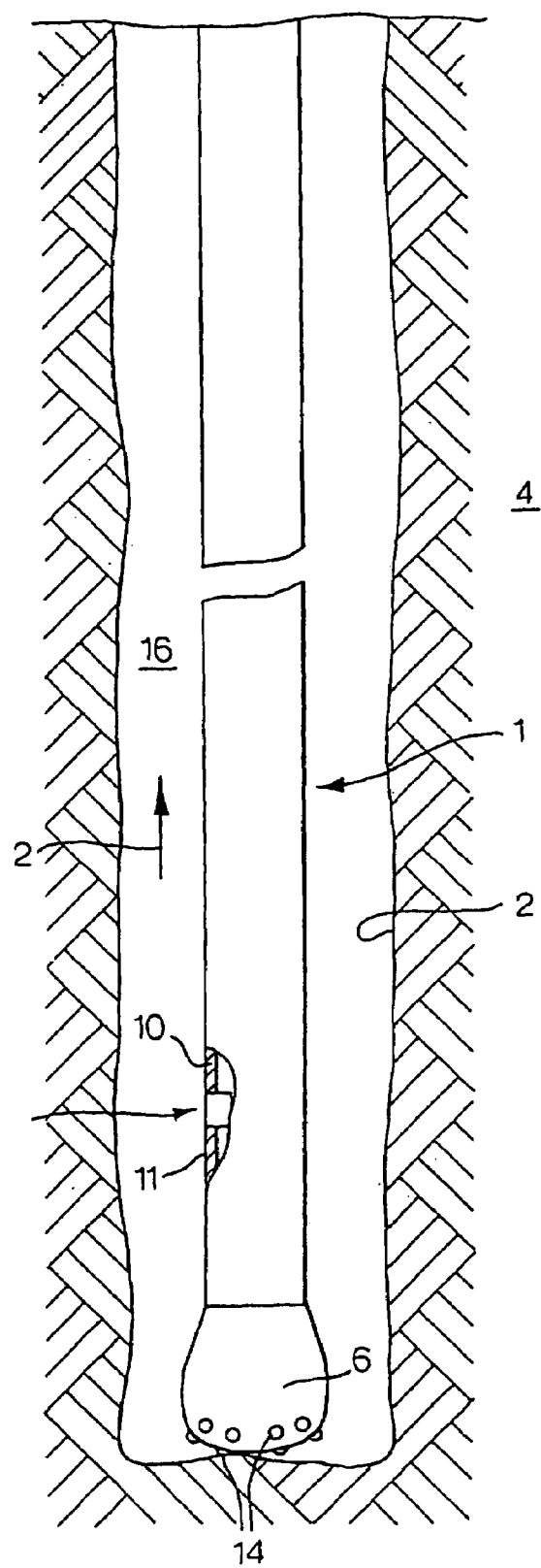
FIG. 1 schematically shows a drill string provided with an embodiment of the system of the invention.

Referring to FIG. 1 there is shown a drill string 1 extending into a wellbore 2 formed in an earth formation 4. The drill string 1 has a drill bit 6 at its lower end, and is provided with a gas detection system 8 suitably arranged in a recess 10 formed in the wall 11 of the drill string 1 a short distance above the drill bit 6. Reference sign 12 indicates a stream of drilling fluid pumped through the drill string 1 to the drill bit 6 where the stream flows via drill bit nozzles 14 into the wellbore 2 and upwardly through the annular space 16 between the wellbore wall and the drill string 1.

As shown in FIG. 2 in more detail, the gas detection system includes a sensor chamber 18 fixedly positioned in the recess 10 of the drill string wall 11. The sensor chamber 18 has a membrane wall 20 with a repelling force for the fluids in the wellbore. The membrane wall 20 is formed of a stack of a hydrophobic (water repelling) membrane 22 and an oleophobic (oil repelling) membrane 24. The membranes 22, 24 are diffusive to gas, i.e. they allow gas to pass from the stream of drilling fluid 12 into the sensor chamber 18 while preventing water (membrane 22) and oil (membrane 24) to flow into the sensor chamber 18. A Micro-Electro-Mechanical-Sensor solid-state sensor 26 ("MEMS sensor") is arranged in the sensor chamber and suitably connected to a control system (not shown) at surface. The sensor 26 is a thermal conductive MEMS pellistor sensor and includes a heat source and a temperature sensor arranged at a selected distance from the heat source.

The sensor chamber 18 is filled with a volume of a selected purge gas. In this example the purge gas is Helium, however it can also be Neon, Argon or any other suitable reference gas.

A supply of Helium is provided in storage vessel 28 with is connected to the chamber 18 by a conduit 30 and control valve 32.

A pressure balancing device 34 is provided to maintain the gas pressure in the sensor chamber 18 substantially equal to the fluid pressure in the stream of drilling fluid 12. The pressure balancing device 34 in accordance with the embodiment shown in FIG. 2 comprises a housing 36 having a liquid chamber 38 and a gas chamber 40 separated from the liquid chamber 38 by a flexible wall 41. The liquid chamber 38 is in fluid communication with the stream of drilling fluid 12 by conduit 42 and the gas chamber 40 is in fluid communication with the interior of the sensor chamber 18 by conduit 43 and conduit 30. An outlet conduit 44 having a control valve 45 provides fluid communication between the sensor chamber 18 and the stream of fluid 12. The flexible wall 40 in the housing 36 is, for example, formed of an elastomer material. The control valves 32, 45 are controlled by a suitable control system (not shown).

FIG. 3 schematically shows an alternative pressure balancing device 74. This embodiment differs from the one described above in that there is no flexible wall provided in the housing 36 separating the liquid 78 from the gas 80. The liquid 80 can be supplied to the housing 36 via an open connection conduit 42, which is optionally provided with a shut-off valve 81. The gas 80 can be the purge gas that is supplied to the interior of sensor chamber 18 via conduits 43 and 30. An outlet conduit 44, optionally having a control valve, provides fluid communication between the sensor chamber 18 and the stream of fluid 12. To ensure proper functioning of this embodiment, the open connection conduit 42 should be connected to the housing 36 in a bottom portion of the housing 36, because the separation of the liquid 78 from the gas 80 relies on gravity.

A pressure balancing device generally can also advantageously be provided in a detection system such as described above having a suitable sensor other than a MEMS sensor.

Figure 4:
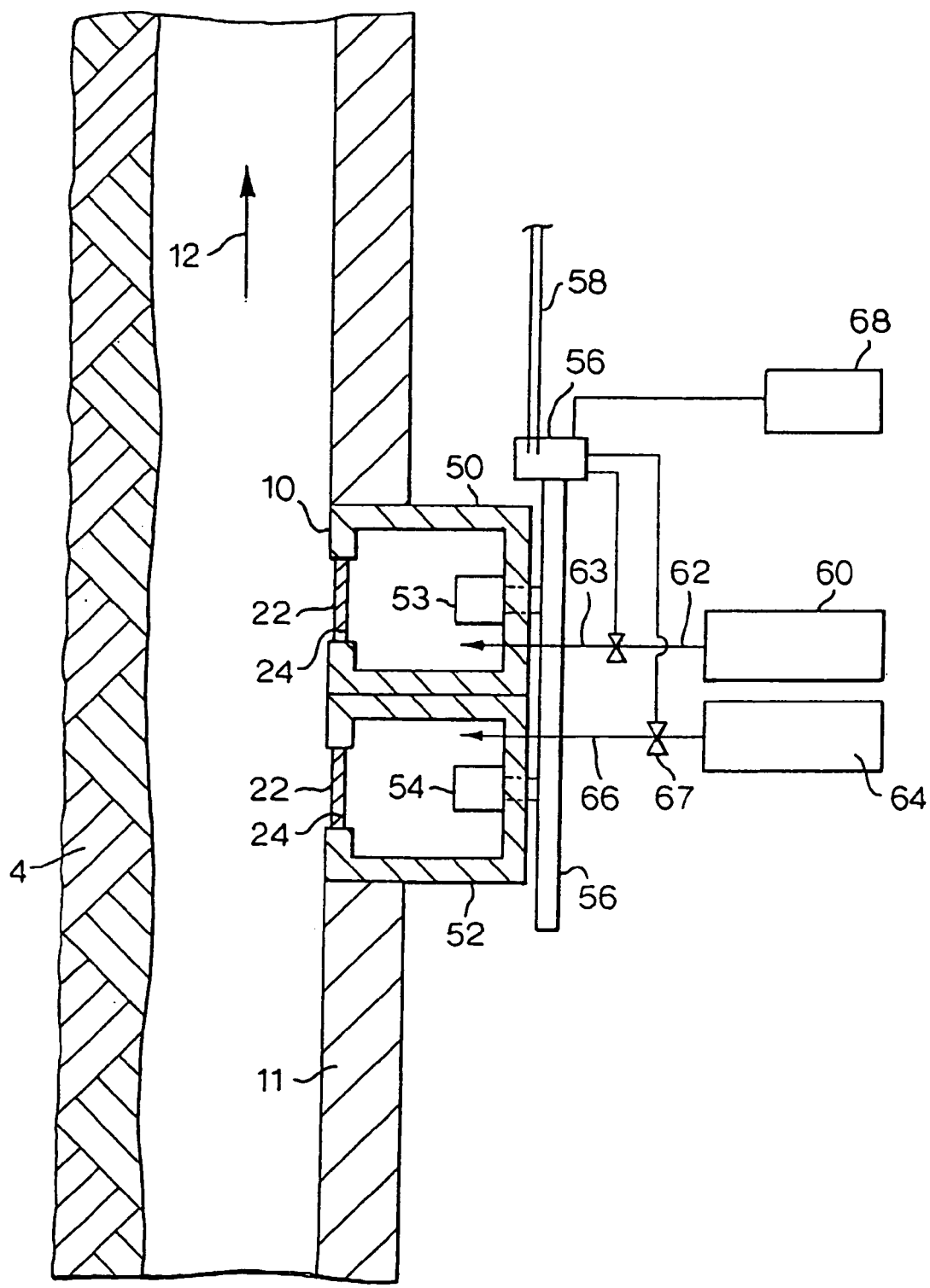
FIG. 4 schematically shows an alternative embodiment of the system of the invention.

In FIG. 4 is shown an alternative embodiment of the system of the invention, wherein a first sensor chamber 50 and an adjacent second sensor chamber 52 are arranged in a recess 10 formed in the drill string wall 11. The first sensor chamber 50 encloses a first MEMS sensor 53 and the second sensor chamber 52 encloses a second MEMS sensor 54. The sensors 53, 54 are connected to a controller 56 which communicates with a suitable control system (not shown) at surface by control line 58. A supply of Helium purge gas is provided in storage vessel 60 with is connected to the first sensor chamber 50 by a conduit 62 and control valve 63, and a supply of Argon purge gas is provided in storage vessel 64 with is connected to the second sensor chamber 52 by a conduit 66 and control valve 67. The control valves 63, 67 are controlled by controller 56 which in turn is controlled by the control system at surface. The controller is powered by a battery 68.

During normal operation of the embodiment of FIGS. 1 and 2 the drill string 1 is rotated in order to further drill the wellbore 2, whereby the stream of drilling fluid 12 is circulated down through the drill string 1 and up through the annular space 16 between the wellbore wall and the drill string 1. The sensor chamber is filled with the selected purge gas Helium. As discussed below, the purge gas is replenished after each formation gas measurement. The MEMS sensor continuously transmits a signal representing the thermal conductivity of the volume of gas present in the sensor chamber 18. The signal will be substantially constant as long as no formation gas enters the sensor chamber 18.

When the wellbore 2 penetrates a formation layer containing gas, such as ethane, carbon dioxide or nitrogen, some of the gas is entrained in the stream of drilling fluid 12 flowing in the annular space 16. The gas can be dissolved in the liquid or can be in the form of gas bubbles if the fluid becomes over saturated with gas. Also the gas can be in the form of large slugs in case the wellbore 2 enters a high-pressure gas reservoir. The partial pressure of each gas component will be higher in the stream of fluid 12 than in the sensor chamber 18 filled with Helium.

Due to the difference in partial pressure of gas in the stream of drilling fluid 12 and the sensor chamber 18, gas present in the stream of drilling 12 will be driven into the sensor chamber 18 through the membranes 22, 24. This applies for every individual gas species diluted in the stream of fluid 12. Water from the stream 12 is prevented from entering the sensor chamber 18 by hydrophobic membrane 22 and oil from the stream 12 is prevented from entering the sensor chamber 18 by oleophobic membrane 24. Upon entering of gas in the sensor chamber 18, the thermal conductivity of the gas environment around the MEMS sensor 26 will change. As a result the output signal of the sensor 26 will change from a level related to that of the purge gas to a level related to the formation gas having entered the sensor chamber 18. The changed signal is indicative of formation gas having entered the sensor chamber 18. Therefore the gas measurement in application of the system of the invention is a differential measurement of a sample gas relative to a reference purge gas. The gas volume in the sensor chamber 18 is relatively small so that only small volume of sample gas from the stream of fluid 12. Consequently the time for analysis is short and only a small volume of purge gas is needed to clean the sensor chamber 18 in preparation of a next measurement.

A number of measurements are taken, whereby after each measurement the sampled gas is removed by opening control valve 32 thereby purging the sensor chamber 18 with Helium from the storage vessel 28.

The pressure balancing device 34,74 ensures that the gas pressure in the sensor chamber 18 is substantially equal to the fluid pressure in the stream of drilling fluid 12. In this manner it is achieved that the membranes 22, 24 are not damaged due to high pressure differences across the membranes 22, 24. Thus, by virtue of the pressure balancing device 34,74 the system can be used in deep well bores at depths of for instance 1 km or more, or 3 km or more, allowing the system to be as close as possible to the lower end of the drill string. Having the system at as close to the lower end of the drill string contributes to the early detection of formation gas originating deep in the well bore.

Moreover, the pressure balancing device 34,74 allows for provision of a relatively thin membrane wall with a relatively large surface area, which is advantageous for minimizing any time delay between the appearance of formation gas in the stream of drilling fluid and the earliest detection of it.

The described embodiment of the pressure balancing device 34 has a liquid chamber 38 communicating with the stream of fluid in the wellbore annulus 16, and a gas chamber 40 communicating with the gas filled sensor chamber 18. By this arrangement pressure communication exists between the gas filled sensor chamber 18 and the fluid filled wellbore annulus 16. At the same time the flexible wall 41 separates the stream 12 from the gas in the sensor chamber 18. Thus, the pressure balancing device 34 separates the fluids in the wellbore from the gas inside the chamber 18.

The described alternative embodiment of the pressure balancing device 74 has a liquid 78 communicating with the stream of fluid in the wellbore annulus 16, and a gas 80 communicating with the gas filled sensor chamber 18. By this arrangement pressure communication exists between the gas filled sensor chamber 18 and the fluid filled wellbore annulus 16. Since there is no flexible wall separating the stream 12 from the gas in the sensor chamber 18, this embodiment is preferred for ensuring that no pressure difference can exist between the liquid and the gas as a result of possible mechanical support that could be provided by a flexible wall. However, in this alternative embodiment, there is a risk that fluid enters the sensor chamber.

In order to compensate for the relatively large gas compression during the first approximately 500 m depth while lowering the system in a wellbore, the purge gas present in the housing 36 can optionally be pre-pressurized with a closed shut-off valve 81. When reaching the approximately 500 m depth the shut-off valve can be opened to achieve the open connection to the wellbore. Herewith the volume required for the gas 80 in the housing 36 can be reduced.

Capillary pressures in the membranes 22, 24 lead to a relatively small pressure difference across the membranes 22, 24. By selecting membranes 22, 24 with very small pores, such pressure difference may range from 2–14 bars. In order to purge the sensor chamber 18 the Helium gas pressure in storage vessel 28 should be higher than the maximal anticipated wellbore pressure.

As a measurement method it may be selected to utilize signal amplitudes whereby, following an initial disturbance, the signal becomes stable after a relative long period of time, i.e. around 80 minutes for each measurement. A more preferred method involves measurement of the slope of the output signal as it changes in time due to diffusion of formation gas into the sensor chamber 18. This is a fast measurement of about 15–20 seconds turnaround time. Each measurement involves alternating purge gas inflow and formation gas inflow, with 15 seconds interval. In order to improve the accuracy statistical averaging can be carried out over large number of data samples. The slope of the output signal is proportional to the partial dissolved gas concentration. Furthermore, free gas in the stream 12 shows a significantly different slope than gas dissolved in the stream 12, so that such difference can be used for recognition of the gas phase, i.e. either gas-in-liquid or as free gas in the drilling fluid return stream from the drill bit 6.

Normal operation of the embodiment of FIG. 4 is substantially similar to normal operation of the embodiment of FIGS. 1, 2 and 3. The main difference is that two different purge gases, Helium and Argon, are used for the respective sensor chambers 50, 52 instead of one purge gas. Initially sensor chamber 50 is filled with Helium and sensor chamber 52 is filled with Argon. When formation gases methane, carbon dioxide and nitrogen enter the sensor chambers 50, 52, the thermal conductivity of the gas volume in sensor chamber 50 changes differently than the thermal conductivity of the gas volume in sensor chamber 52. Thus the sensor signal of sensor 53 changes differently than the sensor signal of sensor 54. Furthermore, the signal changes depend on the concentrations of the respective gas components methane, carbon dioxide and nitrogen. By calibrating the signal from sensor chamber 50 for the gas components methane, carbon dioxide and nitrogen, a first equation is obtained from the measurement at a selected temperature of the sensor internals. A second equation follows by considering that the sum of all concentration of three gas components $CO_2$, $N_2$ and $CH_4$ add up to one. A third equation is obtained by calibrating the signal from sensor chamber 52 for the gas components methane, carbon dioxide and nitrogen. By solving these equations, compositional information can be extracted.

Each sensor 53, 54 has its own electronic settings and gain such that signal levels are optimized for read-out and for solving the set of 3 equations and 3 unknowns. Possibly the 3-gas species detection problem can be reduced to a 1-gas species detection problem by making use of prior knowledge on the well. For instance by assuming that in a certain well the Methane concentration in natural gas is the only variable.

It is also possible to use an expected formation gas, such as $N_2$, $CH_4$, or $H_2S$ in one of the sensor chambers. A chamber filled with that type of gas does not display a change in the selected characteristic of the gas detected by the sensor. If a second sensor chamber does display a change in the selected characteristic at the same time, this is a direct and fast indication that this type of formation gas is present in the stream of drilling fluid.

While the illustrative enibodiments of the invention have been described with particularity, it will be understood that various other modifications will be readily apparent to, and can be easily made by one skilled in the art without departing from the spirit of the invention. Accordingly, it is not intended that the scope of the following claims be limited to the examples and descriptions set forth herein but rather that the claims be construed as encompassing all features which would be treated as equivalents thereof by those skilled in the art to which this invention pertains.

I claim:

1. A system for detecting the presence of formation gas in a stream of drilling fluid flowing through a weilbore during drilling of the welibore, the system comprising at least one sensor chamber connectable to a drill string for drilling the welibore, each sensor chamber containing a sensor and a volume of a selected gas and having a membrane wall which allows passage of formation gas from the stream of drilling fluid into the sensor chamber, the sensor being arranged to detect a change of a selected characteristic of said volume of gas due to passage of formation gas from the stream of drilling fluid via the membrane wall into the sensor chamber.

2. The system of claim 1, wherein said membrane wall substantially prevents passage of liquid from the stream of drilling fluid into the sensor chamber.

3. The system of claim 1, wherein the membrane wall is both hydrophobic and oleophobic.

4. The system of claim 3, wherein the membrane wall is formed of a stack comprising a hydrophobic membrane and an oleophobic membrane.

5. The system of claim 1, wherein the sensor is arranged to detect or measure a change in thermal conductivity of said volume of gas.

6. The system of claims 1, wherein the sensor includes a heat source and a temperature sensor arranged at a selected distance from the heat source, and wherein said volume of gas extends between the heat source and the temperature sensor.

7. The system of claim 1, wherein the sensor is a Micro-Electro-Mechanical-Sensor (MEMS) solid-state sensor.

8. The system of claim 7, wherein the sensor is a conductive MEMS pellistor sensor.

9. The system of claim 1, further comprising a pressure balancing device arranged to maintain the gas pressure in the sensor chamber substantially equal to the fluid pressure in the stream of drilling fluid.

10. The system of claim 9, wherein the pressure balancing device comprises a housing containing a liquid and a gas arranged to exert a force from one to the other, wherein the liquid is in fluid communication with the stream of drilling fluid and the gas is in fluid communication with the sensor chamber.

11. The system of claim 10, wherein the housing comprises a liquid chamber and a gas chamber separated from the liquid chamber by a movable wall, whereby the liquid chamber is in fluid communication with the stream of drilling fluid and the gas chamber is in fluid communication with the sensor chamber.

12. The system of claim 11, wherein said movable wall is a flexible wall.

13. The system of claims 1, further comprising a gas supply device for supplying the sensor chamber with said selected gas.

14. The system of claim 13, wherein the system comprises a first said sensor chamber and a second said sensor chamber, and wherein the gas supply device includes means for supplying a first said selected gas to the first sensor chamber and means for supplying a second said selected gas to the second sensor chamber.

15. The system of claim 13, wherein the gas supply device is arranged to purge each sensor chamber with the corresponding selected gas.

16. A drill string provided with the system of claim 1.

* * * * *